(12) United States Patent
Courel et al.

(10) Patent No.: US 8,597,624 B2
(45) Date of Patent: *Dec. 3, 2013

(54) ORGANOPOLYSILOXANE EMULSIONS AND THEIR PRODUCTION

(75) Inventors: Benedicte Courel, Waterloo (BE); Delphine Davio, Le Roeulx (BE); Andreas Stammer, Pont-A-Celles (BE); Sophie Stassen, Rhode-Saint-Genese (BE)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/260,275

(22) PCT Filed: Mar. 30, 2010

(86) PCT No.: PCT/EP2010/054220
§ 371 (c)(1),
(2), (4) Date: Sep. 24, 2011

(87) PCT Pub. No.: WO2010/115782
PCT Pub. Date: Oct. 14, 2010

(65) Prior Publication Data
US 2012/0020909 A1    Jan. 26, 2012

(30) Foreign Application Priority Data
Mar. 31, 2009    (GB) .................................. 0905502.1

(51) Int. Cl.
*A61Q 5/12* (2006.01)
*A61Q 19/00* (2006.01)
*A61K 8/89* (2006.01)

(52) U.S. Cl.
USPC ........................................................ 424/70.12

(58) Field of Classification Search
None
See application file for complete search history.

(56) References Cited

U.S. PATENT DOCUMENTS

| | | | | |
|---|---|---|---|---|
| 2,891,920 A | * | 6/1959 | Hyde et al. ................ | 524/714 |
| 3,294,725 A | * | 12/1966 | Findlay et al. ............ | 524/745 |
| 3,419,593 A | | 12/1968 | Willing | |
| 3,445,420 A | | 5/1969 | Kookootsedes et al. | |
| 3,715,334 A | | 2/1973 | Karstedt | |
| 3,814,730 A | | 6/1974 | Karstedt | |
| 3,819,530 A | * | 6/1974 | Ratledge et al. ........... | 516/38 |
| 3,839,388 A | | 10/1974 | Nitzsche et al. | |
| 3,923,705 A | | 12/1975 | Smith | |
| 3,989,667 A | | 11/1976 | Lee et al. | |
| 4,311,695 A | * | 1/1982 | Starch ......................... | 514/63 |
| 4,312,801 A | | 1/1982 | Hiriart Bodin et al. | |
| 4,404,035 A | | 9/1983 | Ona et al. | |
| 4,564,693 A | | 1/1986 | Riederer | |
| 4,614,758 A | * | 9/1986 | Schwabe et al. ........... | 524/487 |
| 4,701,490 A | | 10/1987 | Buckhardt et al. | |
| 4,725,658 A | | 2/1988 | Thayer et al. | |
| 4,788,001 A | | 11/1988 | Narula | |
| 4,990,556 A | | 2/1991 | Shimizu et al. | |
| 4,990,561 A | | 2/1991 | Yoshioka | |
| 5,035,832 A | | 7/1991 | Takamura et al. | |
| 5,039,724 A | * | 8/1991 | Demlehner et al. ......... | 524/267 |
| 5,133,897 A | * | 7/1992 | Balzer ......................... | 516/72 |
| 5,175,325 A | | 12/1992 | Brown et al. | |
| 5,189,102 A | * | 2/1993 | Tsubuko et al. ............. | 525/112 |
| 5,262,087 A | * | 11/1993 | Tachibana et al. .......... | 516/23 |
| 5,403,909 A | | 4/1995 | Rubinsztajn | |
| 5,434,215 A | * | 7/1995 | Sankaran et al. ........... | 524/763 |
| 5,457,220 A | | 10/1995 | Razzano | |
| 5,503,755 A | | 4/1996 | Danner | |
| 5,504,150 A | | 4/1996 | Gilson et al. | |
| 5,603,940 A | * | 2/1997 | Candau et al. .............. | 424/401 |
| 5,633,303 A | * | 5/1997 | Kondo et al. ............... | 524/268 |
| 5,830,483 A | * | 11/1998 | Seidel et al. ................ | 424/401 |
| 5,888,485 A | | 3/1999 | O'Lenick, Jr. et al. | |
| 5,914,362 A | | 6/1999 | Brecht et al. | |
| 5,925,469 A | * | 7/1999 | Gee .............................. | 428/447 |
| 5,973,068 A | | 10/1999 | Yamaya et al. | |
| 6,001,928 A | | 12/1999 | Harkness et al. | |
| 6,048,819 A | | 4/2000 | Habimana | |

(Continued)

FOREIGN PATENT DOCUMENTS

| | | |
|---|---|---|
| CN | 1230547 A | 10/1999 |
| EP | 0200916 A2 | 11/1986 |

(Continued)

OTHER PUBLICATIONS

English language abstract for EP 1671673 extracted from the espacenet.com database on Mar. 7, 2012, 30 pages.
English language abstract and translation for JP 2000-026726 extracted from the PAJ database on Mar. 7, 2012, 40 pages.
International Search Report for Application No. PCT/EP2010/054220 dated Oct. 4, 2010, 4 pages.
International Search Report for Application No. PCT/EP2010/054221 dated Jan. 14, 2011, 6 pages.
English language abstract not available for CN 1230547; however, see English language equivalent US 6,048,819. Original document extracted from the espacenet.com database on Jul. 8, 2013, 9 pages, 1998.

(Continued)

*Primary Examiner* — Robert A Wax
*Assistant Examiner* — Olga V Tcherkasskaya
(74) *Attorney, Agent, or Firm* — Howard & Howard Attorneys PLLC

(57) ABSTRACT

This invention relates to aqueous emulsions comprising a polyorganosiloxane and a wax, and to methods of production of such emulsions. The emulsions are of the type oil-in-water. An organopolysiloxane is polymerized in admixture with a molten wax, thereby forming a blend of the wax with an organopolysiloxane of increased molecular weight, and the said blend of polymer and molten wax is emulsified in water in the presence of a surfactant. The emulsions are useful in personal care applications such as on hair, skin, mucous membrane or teeth. The emulsions are also useful in applications such as paints, water based coatings, textile fiber treatment, leather lubrication, fabric softening, fabric care in laundry applications, homecare, release agents and oil drag reduction.

12 Claims, No Drawings

(56) References Cited

U.S. PATENT DOCUMENTS

| | | | |
|---|---|---|---|
| 6,054,548 A | 4/2000 | Currie et al. | |
| 6,258,891 B1* | 7/2001 | Hoxmeier | 524/848 |
| 6,328,983 B1 | 12/2001 | Afriat | |
| 6,362,280 B1* | 3/2002 | Lences et al. | 525/221 |
| 6,448,196 B1 | 9/2002 | Eglin et al. | |
| 6,468,513 B1 | 10/2002 | Murphy et al. | |
| 6,737,444 B1 | 5/2004 | Liu | |
| 7,041,088 B2 | 5/2006 | Nawrocki et al. | |
| 2003/0191244 A1* | 10/2003 | Yu | 525/100 |
| 2004/0210074 A1 | 10/2004 | Hupfield et al. | |
| 2005/0143282 A1 | 6/2005 | Creutz et al. | |
| 2008/0114143 A1* | 5/2008 | Brothers et al. | 528/26 |
| 2009/0042043 A1* | 2/2009 | Joseph et al. | 428/447 |
| 2009/0215944 A1 | 8/2009 | Maton et al. | |
| 2010/0093598 A1* | 4/2010 | Davio et al. | 510/466 |
| 2010/0137454 A1 | 6/2010 | Barmes et al. | |
| 2012/0027708 A1 | 2/2012 | Durand et al. | |
| 2012/0077729 A1 | 3/2012 | Davio et al. | |
| 2012/0269875 A1* | 10/2012 | Tamura et al. | 424/401 |

FOREIGN PATENT DOCUMENTS

| | | |
|---|---|---|
| EP | 0215470 A2 | 3/1987 |
| EP | 0382365 A2 | 8/1990 |
| EP | 0722972 A1 | 7/1996 |
| EP | 0736562 A2 | 10/1996 |
| EP | 0802231 A2 | 10/1997 |
| EP | 0842974 A1 | 5/1998 |
| EP | 1029897 A1 | 8/2000 |
| EP | 1314415 A1 | 5/2003 |
| EP | 1447423 A1 | 8/2004 |
| EP | 1466935 A1 | 10/2004 |
| EP | 1557435 A1 | 7/2005 |
| EP | 1671673 A1 | 6/2006 |
| GB | 895091 A | 5/1962 |
| GB | 918823 A | 2/1963 |
| GB | 2252975 A | 8/1992 |
| JP | 11-222554 A | 8/1999 |
| JP | H08-222554 A | 8/1999 |
| JP | 2000-026726 | 1/2000 |
| JP | 2006-515383 A | 5/2006 |
| WO | WO 01/25389 A1 | 4/2001 |
| WO | WO 01/49774 A2 | 7/2001 |
| WO | WO 01/49789 A2 | 7/2001 |
| WO | WO 01/79330 A1 | 10/2001 |
| WO | WO 03/082356 A2 | 10/2003 |
| WO | WO 2004/084844 A2 | 10/2004 |
| WO | WO 2005/016998 A2 | 2/2005 |
| WO | WO 2006/106362 A1 | 10/2006 |
| WO | WO 2008/043512 A2 | 4/2008 |
| WO | WO 2008/045427 A1 | 4/2008 |
| WO | WO 2008/110590 A1 | 9/2008 |
| WO | WO 2010/115783 A2 | 10/2010 |

OTHER PUBLICATIONS

English language abstract for EP 0215470 extracted from the espacenet.com database on Jul. 8, 2013, 14 pages, 1987.

English language abstract not available for JP H08-325456; however, see English language equivalent US 5,504,150. Orginal document extracted from the espacenet.com database on Jul. 8, 2013, 12 pages, 1996.

English language abstract and machine-assisted English translation for JP 11-222554 extracted from the PAJ database on Jul. 8, 2013, 36 pages, 1999.

English language abstract not available for JP 2006-515383; however, see English language equivalent US 6,737,444. Original document extracted from the espacenet.com database on Jul. 8, 2013, 15 pages, 2006.

H.H. Chuan et al., "Poly(trimethylene terephthalate) molecular weight and Mark- Houwink equation", Polymer 42 (2001) 7137-7139.

International Search Report for Application No. PCT/EP2007/008753 dated May 15, 2008, 3 pages.

International Search Report for Application No. PCT/EP2007/054219 dated Sep. 14, 2007, 4 pages.

International Search Report for Application No. PCT/EP2007/060586 dated Jun. 4, 2008, 3 pages.

International Search Report for Application No. PCT/US2007/021562 dated Feb. 8, 2008, 3 pages.

* cited by examiner

ORGANOPOLYSILOXANE EMULSIONS AND THEIR PRODUCTION

RELATED APPLICATIONS

This application claims priority to and all the advantages of International Patent Application No. PCT/EP2010/054220, filed on Mar. 30, 2010, which claims priority to Great Britain Patent Application No. GB 0905502.1, filed on Mar. 31, 2009.

This invention relates to aqueous emulsions comprising a polyorganosiloxane and a wax, and to methods of production of such emulsions. The emulsions are of the type oil-in-water.

Many personal care products such as face, hand and body crèmes, shampoos, sunscreen formulations and colour cosmetics such as mascara and foundations are emulsions or other dispersions. High molecular weight polyorganosiloxanes are used in many applications in conjunction with organic (non-silicon-containing) ingredients, for example for use in personal care, often providing synergistic effects. The organic ingredients can be waxes or can be incorporated in organic waxes. However polyorganosiloxanes are not compatible (miscible) with many organic ingredients causing problems in obtaining stable dispersions.

WO-A-2006/106362 describes preparing a diluted organopolysiloxane containing polymer by the polycondensation of siloxane containing monomers and/or oligomers which comprise condensable groups in the presence of an organopolysiloxane and/or an organic based diluent material, a suitable catalyst and optionally an end-blocking agent; and where required quenching the polymerisation process. The diluent material is substantially retained within the resulting diluted organopolysiloxane. The diluent needs to be compatible with the organopolysiloxane since otherwise it will exude out of the composition with time. WO-A-2008/045427 describes a method of making a silicone oil-in-water emulsion comprising the further steps of introducing one or more surfactants into the diluted organopolysiloxane to form a homogenous oil phase, adding 0.1-10 percent by weight water to the homogenous oil phase to form a water-in-oil emulsion, applying shear to the water-in-oil emulsion to cause inversion of the water-in-oil emulsion to an oil-in-water emulsion; and optionally diluting the oil-in-water emulsion by adding more water.

U.S. Pat. No. 5,262,087 describes a water-in-oil emulsified composition which comprises a wax composition formed by radical polymerisation of polysiloxanes and wax. Such radical polymerisation will lead to random grafting and crosslinking. JP 2000-026726 describes an emulsion obtained by polymerizing a specified organic silicon compound in the presence of a solvent in an ionic surfactant system. U.S. Pat. No. 5,914,362 describes an emulsion prepared from the reaction of (A) a primary silicone composition and (B) a polydiorganosiloxane having condensable terminal groups in a non polar organic medium selected from polyisobutylene and mineral oil. EP0802231 describes a silicone composition prepared by reacting a mixture comprising (i) mineral oil, (ii) a polyorganosiloxane, (iii) a silicon compound and (iv) a catalytic amount of a catalyst. U.S. Pat. No. 4,990,556 describes a cured silicone rubber containing entrapped mineral oil. Compositions containing organopolysiloxanes and waxes are described in U.S. Pat. No. 4,404,035 and U.S. Pat. No. 5,503,755.

In a method according to the present invention for producing an aqueous emulsion of a polyorganosiloxane and a wax, an organopolysiloxane is polymerized in admixture with a molten wax, thereby forming a blend of the wax with an organopolysiloxane of increased molecular weight, and the said blend of polymer and molten wax is emulsified in water in the presence of a surfactant.

In one preferred procedure the blend of the wax with an organopolysiloxane of increased molecular weight produced in the polymerization reaction is emulsified before the reaction product has cooled to a paste or solid. Alternatively the blend of the wax with an organopolysiloxane of increased molecular weight produced in the polymerization reaction is cooled to a paste or solid and is subsequently heated to melt the wax and emulsified at a temperature above the melting point of the wax.

The blend of wax with organopolysiloxane of increased molecular weight produced in the polymerization reaction is a very intimate dispersion of wax in organopolysiloxane or vice versa. It is of course preferred that this blend is emulsified before any macroscopic phase separation has occurred.

A silicone oil-in-water emulsion according to the invention is characterized in that the disperse phase is a blend of a wax with an organopolysiloxane which has been formed by polymerization in the presence of the wax.

We have found that by emulsifying the blend of wax with high molecular weight organopolysiloxane formed by polymerization in admixture with the wax, stable emulsions of high molecular weight polyorganosiloxanes in conjunction with organic ingredients can more readily be formed.

The organopolysiloxane starting material is preferably an organopolysiloxane containing at least one hydroxyl or hydrolysable group bonded to silicon and is preferably polymerized by a process comprising siloxane condensation. The organopolysiloxane starting material can for example be a substantially linear organopolysiloxane containing on average more than one hydroxyl or hydrolysable group bonded to silicon, preferably terminal hydroxyl or hydrolysable groups. The organopolysiloxane can for example have the general formula $$X^1\text{-}A'\text{-}X^2 \tag{1}$$

where $X^1$ and $X^2$ are independently selected from silicon containing groups which contain hydroxyl or hydrolysable substituents and A' represents a polymer chain. Examples of $X^1$ or $X^2$ groups incorporating hydroxyl and/or hydrolysable substituents include groups terminating as described below:

where each $R^a$ independently represents a monovalent hydrocarbyl group, for example, an alkyl group, in particular having from 1 to 8 carbon atoms, (and is preferably methyl); each $R^b$ and $R^d$ group is independently an alkyl or alkoxy group in which the alkyl groups suitably have up to 6 carbon atoms; $R^c$ is a divalent hydrocarbon group which may be interrupted by one or more siloxane spacers having up to six silicon atoms; and p has the value 0, 1 or 2. Endblocking groups are of the formula $-(R^a)_2SiOH$ may be particularly preferred. The linear organopolysiloxane can include a small amount, for example less than 20%, of unreactive endblocking groups of the formula $R^a_3SiO_{1/2}$.

The polymer chain A' is preferably a polydiorganosiloxane chain comprising siloxane units of formula (2)

in which each $R^2$ is independently an organic group such as a hydrocarbon group having from 1 to 18 carbon atoms, a substituted hydrocarbon group having from 1 to 18 carbon atoms or a hydrocarbonoxy group having up to 18 carbon atoms.

Examples of hydrocarbon groups $R^2$ include methyl, ethyl, propyl, butyl, vinyl, cyclohexyl, phenyl and tolyl groups.

Substituted hydrocarbon groups have one or more hydrogen atoms in a hydrocarbon group replaced with another substituent, for example a halogen atom such as chlorine, fluorine, bromine or iodine, an oxygen atom containing group such as acrylic, methacrylic, alkoxy or carboxyl, a nitrogen atom containing group such as an amino, amido or cyano group, or a sulphur atom containing group such as a mercapto group. Examples of substituted hydrocarbon groups include a propyl group substituted with chlorine or fluorine such as 3,3,3-trifluoropropyl, chlorophenyl, beta-(perfluorobutyl)ethyl or chlorocyclohexyl group. Preferably, at least some and more preferably substantially all of the groups $R^2$ are methyl. Preferably the polydiorganosiloxanes are polydialkylsiloxanes, most preferably polydimethylsiloxanes.

Polydiorganosiloxanes comprising units of the formula (2) may be homopolymers or copolymers. Mixtures of different polydiorganosiloxanes are also suitable. In the case of polydiorganosiloxane co-polymers the polymeric chain may comprise a combination of blocks made from chains of units depicted in FIG. 2 above where the two $R^2$ groups are:
  both alkyl groups (preferably both methyl or ethyl), or
  alkyl and phenyl groups, or
  alkyl and fluoropropyl, or
  alkyl and vinyl or
  alkyl and hydrogen groups.
Typically at least one block will comprise siloxane units in which both $R^2$ groups are alkyl groups.

The substantially linear organopolysiloxane starting material containing at least one hydroxyl or hydrolysable group bonded to silicon generally has a degree of polymerization such that its viscosity is between 5 mPa·s and 5000 mPa·s., preferably between 10 mPa·s and 500 mPa·s. Preferably the substantially linear organopolysiloxane is a polydimethylsiloxane having terminal hydroxyl groups bonded to silicon and having a viscosity between 10 mPa·s and 500 mPa·s.

The polymer (A') used as substantially linear polyorganosiloxane starting material may alternatively have a block copolymeric backbone comprising at least one block of siloxane groups of the type depicted in formula (2) above and at least one block comprising any suitable organic polymer chain. Examples of suitable organic polymer chains are polyacrylic, polyisobutylene and polyether chains.

According to one aspect of the invention such a substantially linear organopolysiloxane containing at least one hydroxyl or hydrolysable group bonded to silicon is polymerized by catalysed condensation of the hydroxyl or hydrolysable groups to form siloxane bonds. The substantially linear organopolysiloxane can for example be substantially the only organopolysiloxane starting material used.

Alternatively the organopolysiloxane starting material can be a cyclic organopolysiloxane, which can be polymerized by a catalysed process of ring opening of the cyclic organopolysiloxane to form siloxane bonds. The cyclic organopolysiloxane used in such a process can for example be octamethylcyclotetrasiloxane or decamethylcyclopentasiloxane.

The cyclic organopolysiloxane can be the only siloxane material in the polymerization reaction or can be used together with an organosilicon material which will react with the ring opened cyclic organopolysiloxane, for example a silane or siloxane material containing at least one hydroxyl or hydrolysable group bonded to silicon. This silane or siloxane material can be for example an organopolysiloxane such as a substantially linear organopolysiloxane containing at least one hydroxyl or hydrolysable group bonded to silicon. If such a substantially linear organopolysiloxane containing at least one hydroxyl or hydrolysable group bonded to silicon and a cyclic organopolysiloxane are polymerized together, they can for example be present in a weight ratio of 10:1 to 1:5 in the polymerization reaction mixture. Polymerisation proceeds by a catalysed process of ring opening of the cyclic organopolysiloxane and condensation of the ring opened product with the substantially linear organopolysiloxane or other silane or siloxane material containing at least one hydroxyl or hydrolysable group bonded to silicon.

According to another aspect of the invention, the organopolysiloxane starting material is a mixture of a substantially linear organopolysiloxane containing at least one hydroxyl or hydrolysable group bonded to silicon and an alkoxysilane having an average of more than two Si-bonded alkoxy groups per molecule. Such a mixture can be polymerized by catalysed siloxane condensation of the substantially linear organopolysiloxane with the alkoxysilane to form a branched organopolysiloxane structure.

The alkoxysilane which is reacted with the linear organopolysiloxane generally contains an average of more than 2 silicon-bonded alkoxy groups per molecule. The alkoxy groups preferably each have 1 to 4 carbon atoms and most preferably are methyl or ethyl groups. The alkoxysilane can for example comprise a trialkoxysilane of the formula R'Si(OR)$_3$, where R represents an alkyl group having 1 to 4 carbon atoms and R' represents a monovalent hydrocarbon or substituted hydrocarbon group having 1 to 18 carbon atoms. Examples of such groups R' include alkyl groups, for example methyl, ethyl, propyl, butyl, hexyl, octyl, 2-ethylhexyl, lauryl or stearyl; cycloalkyl groups, for example cyclopentyl or cyclohexyl); alkenyl groups, for example vinyl, allyl or hexenyl; aryl groups, for example phenyl or tolyl; aralkyl groups, for example 2-phenylethyl; and groups obtained by replacing all or part of the hydrogen in the preceding organic groups with halogen, for example 3,3,3-trifluoropropyl. Examples of preferred trialkoxysilanes include methyltrimethoxysilane, methyltriethoxysilane, isobutyltrimethoxysilane, n-octyltriethoxysilane, n-octyltrimethoxysilane, ethyltrimethoxysilane, ethyltriethoxysilane, vinyltrimethoxysilane, vinyltriethoxysilane, phenyltrimethoxysilane and 3,3,3-trifluoropropyltrimethoxysilane. Trialkoxysilanes having a long chain alkyl group R' having for example 6 to 18 carbon atoms, for example n-octyltrimethoxysilane, react with the linear organopolysiloxane to form a branched organopolysiloxane having a long chain alkyl group, for example an octyl group, at the branching point. The presence of such a long chain alkyl group increases the compatibility of the branched organopolysiloxane with organic materials, for example hydrocarbon solvents or organic polymers.

The alkoxysilane can alternatively be a tetraalkoxysilane such as tetraethoxysilane (tetraethyl orthosilicate). Reaction of the linear organoplysiloxane with a tetraalkoxysilane can form a branched organopolysiloxane having Si-alkoxy functionality in the polysiloxane chain as well as branching.

The alkoxysilane can be a partially condensed alkoxysilane in which some alkoxy groups have been hydrolysed and condensed to form siloxane linkages and some alkoxy groups remain bonded to silicon. Such a partially condensed alkoxysilane preferably contains on average more than two alkoxy groups per molecule bonded to silicon. The alkoxysilane can for example be an oligomeric partially condensed trialkoxysilane. Such an oligomer may have a branched structure as well as Si-alkoxy groups to provide further branching sites. Tetraalkoxysilanes can also be used in partially condensed form; for example partially condensed tetraethoxysilane containing $SiO_2$ branching units is widely available.

The alkoxysilane and the substantially linear organopolysiloxane containing at least one hydroxyl or hydrolysable group bonded to silicon are preferably reacted in amounts such that the molar ratio of Si-bonded alkoxy groups in the alkoxysilane to hydroxyl or hydrolysable groups in the substantially linear organopolysiloxane is from 1:100 to 1:1, more preferably 1:40 to 1:2.

The catalyst for the polymerization of the organopolysiloxane is preferably a phosphazene catalyst. Phosphazene catalysts are effective catalysts both for siloxane condensation and for ring opening polymerization of cyclic organopolysiloxanes. The phosphazene catalyst generally contains at least one —(N=P<)— unit and is usually an oligomer having up to 10 such phosphazene units, for example having an average of from 1.5 up to 5 phosphazene units. The phosphazene catalyst can for example be a halophosphazene, particularly a chlorophosphazene (phosphonitrile chloride), an oxygen-containing halophosphazene, a phosphazene base or an ionic derivative of a phosphazene such as a phosphazenium salt, particularly an ionic derivative of a phosphonitrile halide such as a perchlorooligophosphazenium salt.

One particularly suitable type of phosphazene catalyst is an oxygen-containing halophosphazene, particularly an oxygen-containing chlorophosphazene. Such an oxygen-containing chlorophosphazene can for example have the formula $Cl(PCl_2=N)_n—P(O)Cl$ or $HO(PCl_2=N)_n—P(O)Cl_2$ The average value of n can for example be in the range 1 to 10, particularly 1 to 5. The catalyst may also comprise tautomers of the catalyst of the formula $HO(PCl_2=N)_n—P(O)Cl_2$ Another type of suitable oxygen-containing chlorophosphazene has the formula $Z'O(PCl_2=N)_n—P(O)Cl_2$ in which Z' represents an organosilicon radical bonded to phosphorus via oxygen, for example a phosphazene catalyst of the formula $R''_3SiO(PCl_2=N)_n—P(O)Cl_2$ where each R'' represents a monovalent hydrocarbon or substituted hydrocarbon group having 1 to 18 carbon atoms. The catalyst may also comprise condensation products of such an organosilicon-containing phosphazene. All or some of the chlorine atoms in any of the above oxygen-containing phosphazenes can be replaced by radicals Q, in which Q represents the hydroxyl group, monovalent organic radicals, such as alkoxy radicals or aryloxy radicals, halogen atoms other than chlorine, organosilicon radicals and phosphorus-containing radicals, although this is not preferred.

Another suitable type of phosphazene catalyst is a perchlorooligophosphazenium salt of the formula

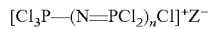

where n has an average value in the range 1 to 10 and Z represents an anion. The anion is preferably a complex anion and can for example be of the formula $MX_{v+1}$ in which M is an element having an electronegativity on Pauling's scale of from 1.0 to 2.0 and valency v and X is a halogen atom. The element M can for example be phosphorus or antimony. The anion Z can alternatively be a complex anion of the formula $[MX_{v-y+1} R^3_y]^-$ wherein $R^3$ is an alkyl group having 1 to 12 carbon atoms and y has a value between 0 and v, as described in U.S. Pat. No. 5,457,220.

The phosphazene catalyst can alternatively be a phosphazene base, particularly an aminated phosphazene as described in U.S. Pat. No. 6,001,928, U.S. Pat. No. 6,054,548 or U.S. Pat. No. 6,448,196. Such a phosphazene base can be formed by reaction of a perchlorooligophosphazenium salt with a secondary amine followed by ion exchange reaction with a basic nucleophile. The secondary amine is for example of the formula $HNR^4_2$, and some or all of the chlorophosphazene oligomer are replaced by —$NR^4_2$ groups.

The phosphazene catalyst is typically present at 1 or 2 up to 200 parts per million based on the weight of organopolysiloxane starting materials, for example at 5 to 50 parts per million. Phosphazene catalysts have the advantage that the content of undesired low molecular weight cyclic silicones in the polymerisation product is low.

Alternative catalysts which can be used for the organopolysiloxane polymerization include any of those known to catalyse siloxane condensation, such as protic acids, Lewis acids, organic and inorganic bases, metal salts and organometallic complexes. Condensation specific catalysts are preferred. These include acidic condensation catalysts of the formula $R^{20}SO_3H$ in which $R^{20}$ represents an alkyl group preferably having from 6 to 18 carbon atoms such as for example a hexyl or dodecyl group, an aryl group such as a phenyl group or an alkaryl group such as dinonyl- or didoecyl-naphthyl, for example the catalyst can be dodecylbenzenesulphonic acid. Other condensation specific catalysts include n-hexylamine, tetramethylguanidine, carboxylates of rubidium or caesium, and hydroxides of magnesium, calcium or strontium.

Further alternative catalysts include condensation catalysts incorporating tin, lead, antimony, iron, cadmium, barium, manganese, zinc, chromium, cobalt, nickel, aluminum, gallium or germanium and zirconium. Examples include metal triflates, organic tin metal catalysts such as triethyltin tartrate, tin octoate, tin oleate, tin naphthate, butyltintri-2-ethyl-hexoate, tinbutyrate, carbomethoxyphenyl tin trisuberate, isobutyltinticeroate, and diorganotin salts especially diorganotin dicarboxylate compounds such as dibutyltin dilaurate, dimethyltin dibutyrate, dibutyltin dimethoxide, dibutyltin diacetate, or dimethyltin bisneodecanoate.

A titanate or zirconate based catalyst can be used, for example a compound according to the general formula $Ti[OR^{22}]_4$ where each $R^{22}$ may be the same or different and represents a monovalent, primary, secondary or tertiary aliphatic hydrocarbon group which may be linear or branched containing from 1 to 10 carbon atoms. The titanate may be chelated, for example with an alkyl acetylacetonate such as methyl or ethyl acetylacetonate.

A further alternative catalyst which might be used as the catalyst in the present invention is any suitable compound providing a source of anions comprising at least one quadrisubstituted boron atom and protons capable of interaction with at least one silanol group as defined in WO 01/79330, for example tetrakis (pentafluoro phenyl) borate anion.

Alternatively polymerization of the organopolysiloxane may be by a hydrosilylation reaction between an unsaturated organic group, for example an alkenyl or alkynyl group, and an Si—H group in the presence of a suitable catalyst. In this route suitable silanes may be utilised as well as siloxane containing monomers and/or oligomers. Thus the organopolysiloxane can comprise an organopolysiloxane containing alkenyl or alkynyl groups which is polymerized with a silane or siloxane material having Si—H groups by a hydrosilylation reaction, or an organopolysiloxane having Si—H groups which is polymerized with an organic compound containing at least two alkenyl or alkynyl groups by a hydrosilylation reaction. The hydrosilylation reaction is generally effected in the presence of a platinum group catalyst.

The organopolysiloxane containing alkenyl or alkynyl groups can be linear or branched, and generally comprises Si-bonded organic groups which are hydrocarbon or substituted hydrocarbon groups containing 1 to 18 carbon atoms, at least two of which are alkenyl or alkynyl groups. The organopolysiloxane may for example contain the alkenyl or alkynyl groups as terminal groups. Each alkenyl or alkynyl group preferably has a terminal double bond. Examples of preferred alkenyl groups are $H_2C=CH—$, $H_2C=CHCH_2—$, $H_2C=C(CH_3)CH_2—$, $H_2C=CHCH_2CH_2—$, $H_2C=CHCH_2CH_2CH_2—$, and $H_2C=CHCH_2CH_2CH_2CH_2—$. Examples of alkynyl groups include $HC≡C—$ and $HC≡CCH_2—$. The other organic groups of the organopolysiloxane can for example be selected from alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. Methyl groups are often preferred. The organopolysiloxane can for example be an alkeyl-terminated linear or branched polydimethylsiloxane.

The organopolysiloxane having Si—H groups can be linear or branched. The other organic groups of the organopolysiloxane can for example be selected from alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. Methyl groups are often preferred. The Si—H groups can be terminal, for example the organopolysiloxane can have dimethylsilyl terminal groups, and/or the Si—H groups can be along the polymer chain, for example the organopolysiloxane can comprise methylhydrogensiloxane units. The organopolysiloxane having Si—H groups can for example be a poly(methylhydrogen)siloxane or a dimethylsiloxane methylhydrogensiloxane copolymer.

If polymerization by hydrosilylation is used, an organopolysiloxane containing alkenyl or alkynyl groups as described above is preferably reacted with an organopolysiloxane having Si—H groups as described above.

The organopolysiloxane containing alkenyl or alkynyl groups can alternatively or additionally be polymerized with a silane containing at least one Si—H group. Examples of such silanes include halosilanes such as trichlorosilane, methyldichlorosilane, dimethylchlorosilane, and phenyldichlorosilane, and alkoxysilanes such as trimethoxy silane, triethoxy silane, methyl diethoxy silane, methyl dimethoxy silane and phenyldimethoxy silane.

The organopolysiloxane containing Si—H groups can alternatively or additionally be polymerized with an organic compound containing at least two alkenyl or alkynyl groups. The alkenyl or alkynyl groups should not be conjugated and are preferably terminal groups. Suitable organic compounds include for example 1,5-hexadiene and 1,7-octadiene.

The catalyst for the hydrosilylation reaction is generally a platinum group catalyst, that is a metal selected from platinum, rhodium, palladium, osmium, iridium, or ruthenium or a compound of one of those metals. Examples of catalysts comprising platinum include chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as $Pt(Al_2O_3)$, platinum black, platinum acetylacetonate, platinous halides exemplified by $PtCl_2$, $PtCl_4$, $Pt(CN)_2$, and complexes of platinous halides with unsaturated compounds exemplified by ethylene, propylene, and organovinylsiloxanes. One preferred platinum catalyst is Karstedt's catalyst, which is a platinum divinyl tetramethyl disiloxane complex typically containing one weight percent of platinum in a solvent such as toluene. Another preferred platinum catalyst is a reaction product of chloroplatinic acid and an organosilicon compound containing terminal aliphatic unsaturation as described in U.S. Pat. No. 3,419,593. A further preferred catalyst is a neutralized complex of platinous chloride and divinyl tetramethyl disiloxane, as described in U.S. Pat. No. 5,175,325.

Examples of hydrosilylation catalyst comprising ruthenium include $RhCl_3(Bu_2S)_3$ and ruthenium carbonyl compounds such as ruthenium 1,1,1-trifluoroacetylacetonate, ruthenium acetylacetonate and triruthinium dodecacarbonyl or a ruthenium 1,3-ketoenolate. Examples of rhodium catalysts include $[Rh(O_2CCH_3)_2]_2$, $Rh(O_2CCH3)_3$, $Rh_2(C_8H_{15}O_2)_4$, $Rh(C_5H_7O_2)_3$, $Rh(C_5H_7O_2)(CO)_2$, and $Rh(CO)[Ph_3P](C_5H_7O_2)$. Examples of iridium catalysts include $IrCOOCCH_3)_3$ and $Ir(C_5H_7O_2)S$.

The concentration of the hydrosilylation catalyst in the composition is usually capable of providing the equivalent of at least 1 part per million of elemental platinum group metal by weight based on the organopolysiloxane. A catalyst concentration providing the equivalent of about 3-50 parts per million of elemental platinum group metal is generally the amount preferred.

Typically, the hydrosilylation polymerisation is carried out using approximately a 1:1 molar ratio of Si—H groups to alkenyl alkynyl groups. The material containing alkenyl groups may be used in slight excess to ensure all the Si—H is consumed in the reaction.

The extent of polymerization during the process of the invention is preferably such that the organopolysiloxane of increased molecular weight produced has a weight average molecular weight Mw at least five times, more preferably at least ten times the weight average molecular weight of the starting organopolysiloxane. The Mw can be measured by gel permeation chromatography (GPC). The Mw of the organopolysiloxane of increased molecular weight produced is preferably at least 50,000, more preferably at least 100,000, and may be as high as 1,000,000 or more.

By a wax we mean a material which is plastic or malleable at temperatures of 15-20° C., has a melting point of at least 20° C., and has a low viscosity when melted. Examples for waxes described in the Kirk-Othmer encyclopaedia of chemical technology (Article on Waxes by Claude Leray, John Wiley & Sons, Inc. 2006). The wax present during the organopolysiloxane polymerization generally has a melting point of above 20° C. and preferably has a melting point in the range 30 to 100° C., more preferably 40 to 90° C. The wax can be an organic wax containing no silicon or can be a silicone wax. For uses in which increasing the compatibility of the organopolysiloxane formulation with organic materials is important, organic waxes are usually preferred although silicone waxes containing long chain organic substituents can also increase compatibility.

The wax can for example be a hydrocarbon wax such as a petroleum-derived wax, particularly a paraffin wax or microcrystalline wax, a Fischer-Tropsch wax, ceresin wax, a polyethylene wax or a mixture thereof. Paraffin waxes contain predominantly straight-chain hydrocarbons with an average chain length of 20 to 30 carbon atoms. Examples of paraffin waxes are sold by IgiWax under the trade mark Parafflex, such as Parafflex 4750 A granules and Parafflex 4797A. Microcrystalline wax contains a higher percentage of branched hydrocarbons and naphthenic hydrocarbons. Examples of microcrystalline waxes are sold by IgiWax under the trade mark Microsere, for example Microsere 5981A. Other organic hydrocarbon waxes that can be used are montan wax (also known as lignite-wax), ozokerite or slag wax.

The wax can alternatively be a wax comprising carboxylic esters. Many natural waxes such as beeswax, lanolin, tallow, carnauba and candelilla, as well as tribehenin and waxes derived from plant seeds, fruits, nuts or kernel, such as palm wax, rice bran wax or soy wax, comprise a mixture of esters with free acids and/or alcohols. Examples of ester waxes are palm waxes derived from palm oil sold by IgiWax under the trade names RD2778A and RD2779A. Some of the softer waxes are referred to as 'butter'. These types of products are—frequently used in skin care applications and are for example derived from oilseeds as mango butter, shea butter or cocoa butter. Other examples are illipe, cupuacu, murumuru, sal and kokum butter. Such a butter can be used as all or part of the wax of the invention, provided that the wax has a melting point of at least 20° C. In general butters can be defined by having a titer point of below 40.5° C. but above 20° C. ("Oils of nature" by J. O'Lenick according to AOCS method Tr 1 a-64T).

The wax can alternatively be a long chain fatty acid, a long chain fatty alcohol, a long chain fatty amine, a long chain fatty amide, an ethoxylated fatty acid or fatty alcohol, or a long chain alkyl phenol. In general the long chain of the fatty acid, alcohol, amine or amide is an alkyl group of at least 12 and preferably at least 16 carbon atoms, often up to 30 or more carbon atoms.

The wax can alternatively be a polyether wax, for example a solid polyether polyol or a waxy polyvinyl ether such as that sold by BASF under the trade mark Lumax V, or a polyetherester.

Examples of silicone waxes are polysiloxanes containing hydrocarbon substituents having 12 or more carbon atoms. The polysiloxane is preferably a polydiorganosiloxane comprising methyl alkyl siloxane units ((CH3) ($R^3$) Si02/2), where $R^3$ is a long chain alkyl group having 12 or more, preferably 16 to 100 carbon atoms, optionally together with dimethyl siloxane units or units of the formula ((CH3) ($R^4$) SiO2/2) where $R^4$ is an alkyl group having 1-11 carbon atoms, for example ethyl, a cycloalkyl group such as 2-cyclohexylethyl, a haloalkyl group, an aryl group such as phenyl or an aralkyl group such as 2-phenylpropyl, 2-phenylethyl or 2-(t-butylphenylethyl). The methyl group of the above siloxane units could be replaced by ethyl or another lower alkyl group if desired. The long chain alkyl group $R^3$ can optionally be substituted by polar substituents such as amino, amido, alcohol, alkoxy, or ester groups. Preferably at least 20% of the silicon atoms in the silicone wax, and most preferably at least 50%, have an alkyl substituent having 16 to 100 carbon atoms, most preferably 20 to 36 carbon atoms.

Mixtures of different types of waxes can be used, for example a blend of an ester wax with a hydrocarbon wax.

The wax can be present during the polymerization in any amount from 1 or 5% based on the organopolysiloxane up to 150 or 200% based on the organopolysiloxane. Preferably the weight ratio of organopolysiloxane to wax present during the polymerization is from 95:5 to 40:60. The wax can be melted before contacting the organopolysiloxane, or solid wax can be mixed with the organopolysiloxane and heated to melt the wax while applying shear to mix.

The polymerization of the organopolysiloxane is carried out at a temperature above the melting point of the wax. Preferably the temperature of polymerization is from 5° C. to 30° C. above the melting point of the wax, for example the temperature of polymerization can be in the range 50° C. to 120° C. Most waxes, particularly organic waxes such as hydrocarbon waxes and ester waxes, are not miscible with organopolysiloxanes such as a hydroxyl-tipped polydimethylsiloxane. The wax and the silicones are thus present as a liquid/liquid dispersion and the polymerisation is therefore a dispersion polymerization.

The polymerization reaction can be terminated when a desired degree of polymerization has been reached. This can be determined for example by monitoring the viscosity of the polymerization reaction mixture or the torque required to mix it. Polymerisation catalysed by the preferred phosphazene catalysts can be terminated by adding a neutralizing agent, for example a trialkylamine such as trihexylamine in the case of the catalysts described in U.S. Pat. No. 5,457,220. The time for which polymerization is carried out can be varied within wide limits, for example from 1 or 2 minutes up to 10 hours or more. Polymerisation catalysed by the preferred phosphazene catalysts is usually carried out for 2 to 150 minutes.

An inert liquid diluent can be present during the polymerization if desired. A diluent can be a silicone based and/or organic based diluent and is generally chosen to have no groups reactive with the organopolysiloxane. The diluent if used will usually be chosen from materials whose presence is desired as an extender or plasticizer in the end product formulation based on the wax silicone blend produced.

Any suitable diluent or combination of diluents may be used in the reaction mixture. In general any of the extenders used in WO-A-2006/106362 can be used. These include each of the following alone or in combination with others from the list:

hydrocarbon oils such as mineral oil fractions comprising linear (e.g. n-paraffinic) mineral oils, branched (iso-paraffinic) mineral oils, and/or cyclic (referred in some prior art as naphthenic) mineral oils, the hydrocarbons in the oil fractions comprising from 5 to 25 carbon atoms per molecule;

trialkylsilyl terminated polydialkyl siloxane where the alkyl groups are preferably methyl groups, where each alkyl group may be the same or different and comprises from 1 to 6 carbon atoms but is preferably a methyl group, preferably with a viscosity of from 100 to 100000 mPa·s at 25° C. and most preferably from 1000 to 60000 mPa·s at 25° C.;

polyisobutylenes (PIB);

phosphate esters such as trioctyl phosphate;

polyalkylbenzenes, linear and/or branched alkylbenzenes such as heavy alkylates, dodecyl benzene and other alkylarenes;

esters of aliphatic monocarboxylic acids;

linear or branched mono unsaturated hydrocarbons such as linear or branched alkenes or mixtures thereof containing from 8 to 25 carbon atoms;

natural oils and derivatives thereof.

Preferred diluents include the mineral oil fractions, alkylcycloaliphatic compounds and alkybenzenes including polyalkylbenzenes. Any suitable mixture of mineral oil fractions may be used as diluent but high molecular weight extenders, for example having a molecular weight above 220, are particularly preferred. Examples include alkylcyclohexanes of molecular weight above 220), paraffinic hydrocarbons and mixtures thereof containing from 1 to 99%, preferably from 15 to 80% n-paraffinic and/or isoparaffinic hydrocarbons (linear branched paraffinic) and 1 to 99%, preferably 85 to 20% cyclic hydrocarbons (naphthenic) and a maximum of 3%, preferably a maximum of 1% aromatic carbon atoms. The cyclic paraffinic hydrocarbons (naphthenics) may contain cyclic and/or polycyclic hydrocarbons.

Alternative preferred diluents suitable for retaining in many products as an extender or plasticiser comprise non-mineral based natural oils, i.e. oils derived from animals, seeds or nuts and not from petroleum. Such natural oils are generally triglycerides of mixtures of fatty acids, particularly mixtures containing some unsaturated fatty acid. Diluents containing natural oils may for example be preferred for use in some personal care products. The diluent can be a derivative of a natural oil such as a transesterified vegetable oil, a boiled natural oil, a blown natural oil, or a stand oil (thermally polymerized oil).

The amount of diluent, if used, can for example be up to 60%, usually 5 to 40%, of the combined weight of wax, organopolysiloxane and diluent. The diluent may be miscible with either the siloxane, the molten wax phase of both of them. Many diluents are miscible with the wax and will reduce the melting point of the wax, although the amount of diluent is preferably not so much that the mixture of wax and diluent has a melting point below 20° C.

Any suitable surfactant or combination of surfactants may be used in emulsifying the wax silicone dispersion. The emulsion produced can be either of the oil-in-water (o/w) or water-in-oil (w/o) type. The surfactant can in general be a non-ionic surfactant, a cationic surfactant, an anionic surfactant, or an amphoteric surfactant. The amount of surfactant used will vary depending on the surfactant, but generally is up to about 30 wt. % based on the polydiorganosiloxane, for example 0.2 to 20%.

Examples of nonionic surfactants include condensates of ethylene oxide with long chain fatty alcohols or fatty acids such as a $C_{4-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers and alkylpolysaccharides, for example materials of the structure $R^{24}O$—$(R^{25}O)s$-$(G)_t$ wherein $R^{24}$ represents a linear or branched alkyl group, a linear or branched alkenyl group or an alkylphenyl group, $R^{25}$ represents an alkylene group, G represents a reduced sugar, s denotes 0 or a positive integer and t represent a positive integer as described in U.S. Pat. No. 5,035,832. Alternative nonionic surfactants include polymeric surfactants such as polyvinyl alcohol (PVA) and polyvinylmethylether. Surfactants containing silicon atoms can also be used.

Representative examples of suitable commercially available nonionic surfactants include polyoxyethylene fatty alcohols sold under the tradename BRIJ by Uniqema (ICI Surfactants), Wilmington, Del. Some examples are BRIJ 35 Liquid, an ethoxylated alcohol known as polyoxyethylene (23) lauryl ether, and BRIJ 30, another ethoxylated alcohol known as polyoxyethylene (4) lauryl ether. Similar materials are sold by Croda Europe under the trade marks Volpo L23 and Volpo L4. Some additional nonionic surfactants include ethoxylated alcohols sold under the trademark TERGITOL by The Dow Chemical Company, Midland, Mich., such as TERGITOL TMN-6, an ethoxylated alcohol known as ethoxylated trimethylnonanol; and various ethoxylated alcohols, i.e., C12-C14 secondary alcohol ethoxylates, sold under the trademarks TERGITOL 15-S-5, TERGITOL 15-S-12, TERGITOL 15-S-15, and TERGITOL 15-S-40.

Examples of suitable amphoteric surfactants include imidazoline compounds, alkylaminoacid salts, and betaines. Specific examples include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds.

Examples of cationic surfactants include quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines. Other representative examples of suitable cationic surfactants include alkylamine salts, sulphonium salts, and phosphonium salts.

Examples of suitable anionic surfactants include alkyl sulphates such as lauryl sulphate, polymers such as acrylic acid/$C_{10-30}$ alkyl acrylate crosspolymer, alkylbenzenesulfonic acids and salts such as hexylbenzenesulfonic acid, octylbenzenesulfonic acid, decylbenzenesulfonic acid, dodecylbenzenesulfonic acid, cetylbenzenesulfonic acid and myristylbenzenesulfonic acid; the sulphate esters of monoalkyl polyoxyethylene ethers; alkylnapthylsulfonic acid; alkali metal sulforecinates, sulfonated glyceryl esters of fatty acids such as sulfonated monoglycerides of coconut oil acids, salts of sulfonated monovalent alcohol esters, amides of amino sulfonic acids, sulfonated products of fatty acid nitriles, sulfonated aromatic hydrocarbons, condensation products of naphthalene sulfonic acids with formaldehyde, sodium octahydroanthracene sulfonate, alkali metal alkyl sulphates, ester sulphates, and alkarylsulfonates. Anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

The above surfactants may be used individually or in combination.

The polymerisation catalyst may additionally be the surfactant, or one of the surfactants, involved in the emulsification process. A family of catalysts which can act as surfactants are acidic condensation catalysts of the formula $R^{20}SO_3H$, for example dodecylbenzenesulphonic acid.

In a preferred procedure the blend of the wax with an organopolysiloxane of increased molecular weight produced in the polymerization reaction is emulsified by mixing with surfactant and water before the reaction product has cooled to a paste or solid. Alternatively the blend of the wax with an organopolysiloxane of increased molecular weight produced in the polymerization reaction can be cooled below the solidification temperature of the wax, for example down to room temperature. This yields a paste or solid blend of the wax and the polymerized organopolysiloxane depending on the silicone to wax ratio, the hardness of the wax and the molecular weight of the organosiloxane. The paste or solid is a very intimate dispersion of wax in organopolysiloxane or vice versa. This paste or solid can be reheated to a temperature above the melting point of the wax in the dispersion, and emulsified by mixing with surfactant and water.

In one preferred emulsification procedure according to the invention, emulsification is carried out by mixing the reaction product with 0.5 to 20% by weight of water in the presence of 1 to 30% by weight surfactant, followed by at least one step of mixing the resulting emulsion with water until the desired concentration of emulsified wax organopolysiloxane blend in water is reached. The amount of water present in the initial mixing step of the emulsification can for example be 1 to 10% based on the polymerization reaction product. In such a procedure in which only a small amount of water is initially added to the polymerization reaction product, a water-in-oil emulsion containing a continuous wax/silicone phase and a dispersed water phase can be formed, particularly if the amount of water is less than 5%. By applying shear to the water-in-oil emulsion, a phase inversion of the water-in-oil emulsion to a viscous oil-in-water emulsion is effected. The high shear mixing is preferably carried out in a mixer designed to deal with thick pastes such as a dental mixer. Further additions of small amounts of water with high shear mixing may be carried out before optionally diluting the oil-in-water emulsion by adding more water under lower shear.

The particle size of the emulsion can for example be within the range 0.1 to 100 μm. The quantity of water and surfactant used in the initial phase inversion process may have an impact on the particle size of the final emulsion. For instance, if an emulsion is formed with the same quantity of water in two instances but in the first a large quantity of water is mixed before the phase inversion step and in the second a small quantity of water is mixed before the phase inversion step followed by mixing the remaining additional water after the phase inversion step, the first emulsion will generally have a larger particle size than the second. No matter how the water is added, the total amount of water used is generally between about 1 and 99 wt. %, preferably between about 6 and about 99 wt. %, based on the weight of the emulsion.

Formulations containing the dispersion of polyorganosiloxane and wax can contain various additives known in silicone formulations, for example "active materials" such as perfumes, sunscreens, vitamins, antioxidants, drugs, biocides, pest repellents, catalysts, natural extracts, peptides, warming effect and cooling agents, or fillers, colouring agents such as dyes, pigments and shimmers, heat stabilizers, flame retardants, UV stabilizers, fungicides, biocides, thickeners, preservatives, antifoams, freeze thaw stabilizers, or inorganic salts to buffer pH. Such materials can be added to the mixture of organopolysiloxane and wax before, during or after polymerisation. If added after polymerisation, they can be added before or after the reaction product has been emulsified.

The "active material" is an organic material intended to have an effect in the formulation in which the polymerised organopolysiloxane is used. High molecular weight silicones are used in household care and personal care applications often in conjunction with organic active material ingredients such as perfumes or essential oil. Often, significant amounts of the costly active material, for example perfume, are wasted during the application not contributing to the end users benefit. We have found that by polymerizing the organopolysiloxane in the presence of a wax according to the invention, we can incorporate perfume in the blend of wax and polymerized organopolysiloxane yielding shelf stable products which release the perfume only slowly, and may be controlled to release the perfume or other active material in desired circumstances. Controlled release can be achieved particularly if the active material is added before, during or after polymerisation, but before the reaction product has been emulsified.

One example of an active material is a fragrance composition (perfume). The fragrance composition may be solid or liquid and may be a single fragrant compound, or a natural scented oil, or may be a mixture of fragrant compounds and/or natural oils. Examples of such natural oils and fragrant compounds are described in WO-A-01/25389; these natural oils and fragrant compounds are in particular those suitable for use in cleaning compositions for household or personal use, for example a powder or liquid laundry detergent, a fabric softener or an ironing aid, or for air fresheners. The fragrance composition may alternatively be a perfume for incorporation in a personal care product such as a skin cream, shampoo or face cream, or a colour cosmetics product such as a foundation or mascara, or may be a flavour or aroma compound to be applied for example to food or food packaging. The fragrance composition can alternatively comprise a chemically protected fragrance compound such as a reaction product of the fragrance compound.

Perfumes generally dissolve easily in molten organic waxes. The perfume can be mixed with the wax and then heated to melt the wax, or the wax can be melted and then mixed with the perfume, or the molten wax can be mixed with the organopolysiloxane starting material and then mixed with the perfume. Alternatively the perfume can be mixed with the polysiloxane and wax during the polymerization reaction, that is after the catalyst has been added, or with the reaction product while the wax is still molten.

Alternative type of active material which can be incorporated in the wax silicone composition include sunscreen materials, antioxidants, vitamins, insect repellents and warming effect and cooling agents (materials which give a warming or cooling sensation to the skin). Examples of sunscreens include those which absorb ultraviolet light between about 290-320 nanometers (the UV-B region) such as para-aminobenzoic acid derivatives and cinnamates such as octyl methoxycinnamate or 2-ethoxyethyl p-methoxycinnamate; and those which absorb ultraviolet light in the range of 320-400 nanometers (the UV-A region) such is benzophenones and butyl methoxy dibenzoylmethane. Examples of vitamins are vitamins A and E, retinol and tocopherol. Menthol is an example of a cooling agent. These materials can be used in personal care products. Sunscreens and vitamins are used in skin creams and lotions and are released only slowly if they have been incorporated in a wax silicone blend according to the invention. Cooling agents incorporated in a wax silicone blend can be used in a skin care composition to give prolonged release of the cooling agent when the composition is rubbed into the skin. Insect repellent personal care products can for example be in the form of creams, sticks or sprays, and controlled release of the insect repellent from the personal care product is required after the product has been applied to the skin.

The invention can also be used to give controlled release of a drug (a pharmaceutically active material) by incorporating the drug in a wax silicone blend according to the invention and using this blend in a composition which is applied to the skin to dose the drug by transdermal delivery.

A further alternative type of active material which can be incorporated in the wax silicone blend is a biocide, for example to give prolonged protection against bacterial degradation of a composition including the blend or to give a prolonged biocidal effect to a substrate to which the composition has been applied.

A further alternative type of active material which can be incorporated in the wax silicone blend is a catalyst. A wax silicone blend in which a curing catalyst has been incorporated can for example be used in coatings or adhesives where controlled release is advantageous to give thorough cure without curing too rapidly.

The wax can be chosen so that the active material is released in response to a change in temperature or in the environment encountered by the wax silicone blend. For example the melting point of the wax can be chosen so that the perfume is released above the ironing temperature when the wax silicone blend is used in products for ironing aid. Alternatively the wax can be sparingly soluble in water so that the perfume is slowly released when the wax silicone blend is used in a product applied in water, for example in fabric softener. Polyethylene glycol polyether waxes for example are sparingly soluble in water.

The emulsions of the invention are useful in personal care applications such as on hair, skin, mucous membrane or teeth. In these applications, the silicone is lubricious and will improve the properties of skin creams, skin care lotions, moisturisers, facial treatments such as acne or wrinkle removers, personal and facial cleansers such as shower gels, liquid soap, hand sanitizers and wipes, bath oils, perfumes, fragrances, colognes, sachets, deodorants, sun protection creams, lotions and wipes, colour cosmetics such as foundations and mascaras, self tanning creams, lotions and wipes, pre-shave and after shave lotions, after sun lotion and creams, antiperspirant sticks, soft solid and roll-ons, shaving soaps and shaving lathers. It can likewise be use in hair shampoos, rinse-off and leave-on hair conditioners, hair styling aids, such as sprays, mousses and gels, hair colorants, hair relaxers, permanents, depilatories, and cuticle coats, for example to provide styling and conditioning benefits. In cosmetics, the silicone functions as a levelling and spreading agent for pigment in make-ups, colour cosmetics, compact gel, cream and liquid foundations (water-in-oil and oil-in-water emulsions, or anhydrous lotions), blushes, eye liners, eye shadows, mascaras, and make up removers. The emulsion of silicone and wax is likewise useful as a delivery system for oil and water soluble substances such as vitamins, fragrances, emollients, colorants, organic sunscreens, or pharmaceuticals. When the emulsion is used in personal care products, the polyorganosiloxane generally comprises about 0.01 to about 50 weight percent, preferably 0.1 to 25 wt. percent, of the personal care product.

The emulsions produced according to the invention are also useful in other applications such as paints, water based coatings, textile fibre treatment, leather lubrication, fabric softening, fabric care in laundry applications, homecare, release agents, and oil drag reduction, and in other areas where silicone emulsions are conventionally used. The wax/silicone dispersions have particular advantages in oil drag reduction resulting from increased compatibility with hydrocarbon fluids, especially when the wax is a hydrocarbon wax.

The invention is illustrated by the following Examples, in which parts and percentages are by weight. Catalyst levels given in ppm and are based on the polysiloxane content.

The molecular weight of the siloxanes in the blends was determined by gel permeation chromatography (GPC). The analyses have been performed by GPC (Alliance Waters 2690) using triple detection (Refractive index detector, Viscometer and Light Scattering Detectors) and toluene as solvent. Molecular weight averages were determined by universal calibration relative to a triple detection calibration realized on a single point using polystyrene narrow standard (Mw 70,950 g/mol).

The consistency of cooled blends was tested with a needle penetrometer according to ASTM D217-97 at 25° C. and results are reported in mm/10*3 sec.

Example 1

20 parts Dow Corning HY-3050 soy wax having a melting point of about 55° C. was and mixed and melted at 80° C. with 80 parts of a dimethyl hydroxyl terminated polydimethylsiloxane (having a viscosity of 70 mPa·s at 25° C. measured with a Brookfield LV DV-E viscometer, a Mn of 2500 g/mol and a Mw of 3500 g/mol) to form a liquid/liquid dispersion. 30 parts per million (ppm) of the ionic phosphazene $[Cl(PCl_2=N)_xPCl_3]^+[PCl_6]^-$ diluted in dichloromethane was added as catalyst. The polymerisation was carried out in a 1 l glass reactor at 80° C. under vacuum. The polymerisation was stopped, by the addition of 0.012 parts of trihexylamine, after 14 minutes. The polymerised polydimethylsiloxane has Mn 96 kg/mol and Mw 131 kg/mol.

An emulsion was prepared by adding 0.8 g Volpo L4 and 1.2 g Volpo L23 polyoxyethylene lauryl ether non-ionic surfactants and 1 g water to 20 g of the above dispersion at 80° C. and mixing for 20 seconds at 3000 rpm in a Hausschild dental mixer. An additional 1.0 g of water was added and mixing repeated under the same conditions. Addition of 1.0 g water and mixing was repeated 4 more times. Further additions of water and subsequent mixing were carried out until 18 g water had been added in total, yielding a milky white emulsion with 50% active content. The so obtained emulsion has a particle size of D(v, 0.5) μm=0.61 and D(v, 0.9) μm=1.13 (determined using a Malvern Mastersizer 2000)

Example 2

20 parts of Dow Corning HY-3050 soy wax was mixed and melted at 60° C. with 60 parts of the dimethyl hydroxyl terminated polydimethylsiloxane of Example 1 and 20 parts 'Gemseal 25' (supplied by Total) cosmetic grade mineral oil to form a liquid/liquid dispersion. 30 ppm $[Cl(PCl_2=N)_xPCl_3]^+[PCl_6]^-$ diluted in dichloromethane was added as catalyst. The polymerisation was carried out in a 1 l glass reactor at 60° C. under vacuum. The polymerisation was stopped, by the addition of 0.009 parts of trihexylamine, after 31 minutes. The polymerised polydimethylsiloxane has Mn 73 kg/mol and Mw 103 kg/mol.

An emulsion was prepared by adding 2 g Lutensol T08 ethoxylated oxo alcohol non-ionic surfactant sold by BASF and 1 g water to 25 g of the above dispersion at 60° C. and mixing for 20 seconds at 3000 rpm in a Hausschild dental mixer. An additional 1.0 g of water was added and mixing repeated under the same conditions. Addition of 1.0 g water and mixing was repeated 3 more times yielding a cream with 80% (silicone plus organics) active content. The cream obtained has a particle size of D(v, 0.5) μm=0.28 and D(v, 0.9) μm=0.50 (determined using a Malvern Mastersizer 2000).

Example 3

20 parts of a Candelilla wax having a melting range of about 68.5-72.5° C. (supplied under the name SP75 from Strahl & Pitsch) was melted at 75° C. and mixed at 75° C. with 80 parts of the dimethyl hydroxyl terminated polydimethylsiloxane of Example 1 to form a liquid/liquid dispersion. 20 ppm $[Cl(PCl_2=N)_xPCl_3]^+[PCl_6]^-$ diluted in dichloromethane was added as catalyst. The polymerisation was carried out in a 1 l glass reactor at 75° C. under vacuum. The polymerisation was stopped after 29 minutes, by the addition of 0.013 parts of trihexylamine, A liquid/liquid dispersion i.e. an emulsion of the wax and high molecular weight polydimethylsiloxane was produced and was cooled to room temperature The polymerised polydimethylsiloxane has Mn 221 kg/mol and Mw 285 kg/mol. The dispersion had a penetration of 19 mm/10*3 sec.

Example 4

The polymerisation reaction of Example 1 was repeated using 10 parts Dow Corning HY-3050 soy wax and 90 parts dimethyl hydroxyl terminated polydimethylsiloxane at 70° C. using 10 ppm catalyst. The reaction was stopped after 2 minutes by the addition of 0.008 parts of trihexylamine. The polymerised polydimethylsiloxane has Mn 467 kg/mol and Mw 567 kg/mol. The dispersion was stored at 70° C. during 4 hours and cooled down to room temperature without showing any signs of macroscopic phase separation. The dispersion had a penetration of 40 mm/10*3 sec.

Example 5

20 parts of a shea butter having a melting range of about 28-38° C. (supplied under the name HY-3003 from Dow Corning) was mixed and melted at 70° C. with 80 parts of the dimethyl hydroxyl terminated polydimethylsiloxane of Example 1 to form a liquid/liquid dispersion. 10 ppm [Cl $(PCl_2=N)_xPCl_3]^+[PCl_6]^-$ diluted in dichloromethane was added as catalyst. The polymerisation was carried out in a 1 l glass reactor at 70° C. under vacuum. The polymerisation was stopped after 2 minutes, by the addition of 0.007 parts of trihexylamine, A liquid/liquid dispersion of the butter and high molecular weight polydimethylsiloxane was produced and was cooled to room temperature forming a paste. The polymerised polydimethylsiloxane produced has Mn 383 kg/mol and Mw 464 kg/mol. The dispersion had a penetration of 56 mm/10*3 sec.

Facial creams of the water in oil emulsion type were prepared using the blends prepared in Examples 3 to 5. The formulations are given in the following table.

| Ingredients | INCI | a (%) | b (%) | c (%) |
|---|---|---|---|---|
| Phase A | | | | |
| Dow Corning ® 5200 Formulation Aid | Lauryl PEG/PPG-18/18 Methicone | 2.00 | 2.00 | 2.00 |
| Dow Corning ® FZ-3196 | Caprylyl Methicone | 12.00 | 12.00 | 12.00 |
| Cetiol CC | Dicaprylyl Carbonate | 12.00 | 12.00 | 12.00 |
| polysiloxane-in-Candelilla Wax | Example 3 | 4.00 | — | — |
| polysiloxane-in-Soy Wax | Example 4 | — | 4.00 | — |
| polysiloxane-in-Shea Butter | Example 5 | — | — | 4.00 |
| Phase B | | | | |
| Water | Water | 64.00 | 64.00 | 64.00 |
| Glycerin | Glycerin | 5.00 | 5.00 | 5.00 |
| Sodium Chloride | Sodium Chloride | 1.00 | 1.00 | 1.00 |

PEG = polyethylene glycol,
PPG = polypropylene glycol

The following procedure was used:
1. Mix phase A ingredients together and heat to 85° C. under water bath until melted
2. Mix phase B ingredients together and heat to 85° C.
3. Slowly add phase B to phase A at 1000 rpm
4. When all phase B is added, mix for an additional 5 minutes at 1800-2000 rpm
5. Let cool down to room temperature mixing slowly All the facial cream formulations were homogenous and stable for at least 1 month at room temperature and at 40° C.

The invention claimed is:

1. A method of producing an aqueous emulsion of a polyorganosiloxane and a wax, wherein an organopolysiloxane is polymerized in an admixture with a molten wax, thereby forming a blend of the wax with an organopolysiloxane of increased molecular weight, and the blend of polymer and molten wax is emulsified in water in the presence of a surfactant, wherein the organopolysiloxane is a substantially linear organopolysiloxane containing at least one hydroxyl or hydrolysable group bonded to silicon and is polymerized by catalysed condensation of the hydroxyl or hydrolysable group(s) to form siloxane bonds or wherein the organopolysiloxane comprises a cyclic organopolysiloxane and is polymerized by a catalysed process of ring opening of the cyclic organopolysiloxane to form siloxane bonds.

2. The method according to claim 1, wherein the organopolysiloxane is a mixture of a substantially linear organopolysiloxane containing at least one hydroxyl or hydrolysable group bonded to silicon and an alkoxysilane having an average of more than two alkoxy groups per molecule, and is polymerized by catalysed siloxane condensation of the substantially linear organopolysiloxane with the alkoxysilane to form a branched organopolysiloxane structure.

3. The method according to claim 1, wherein the substantially linear organopolysiloxane is a polydimethylsiloxane having terminal hydroxyl groups bonded to silicon and having a viscosity between 10 mPa·s and 500 mPa·s.

4. The method according to claim 1, wherein the polymerization is catalysed by a phosphazene catalyst, a Lewis acid or base.

5. The method according to claim 1, wherein the wax has a melting point in the range 30 to 80° C.

6. The method according to claim 1, wherein the wax is a hydrocarbon wax, an ester wax or a silicone wax.

7. The method according to claim 1, wherein the weight ratio of organopolysiloxane to wax present during the polymerization is from 95:5 to 40:60.

8. The method according to claim 1, wherein the surfactant is a nonionic surfactant.

9. The method according to claim 1, wherein the blend of the wax with an organopolysiloxane of increased molecular weight produced in the polymerization reaction is emulsified before the reaction product has cooled to a paste or solid.

10. The method according to claim 1, wherein the blend of the wax with an organopolysiloxane of increased molecular weight produced in the polymerization reaction is cooled to a paste or solid and is subsequently heated to melt the wax and emulsified at a temperature above the melting point of the wax.

11. The method according to claim 1, wherein the emulsification is carried out by mixing the blend of polymer and wax with 1 to 20% by weight of water in the presence of 1 to 30% by weight surfactant, followed by at least one step of mixing the resulting emulsion with water until the desired concentration of emulsified wax organopolysiloxane blend in water is reached.

12. A method of producing an aqueous emulsion of a polyorganosiloxane and a wax, wherein an organopolysiloxane is polymerized in an admixture with a molten wax, thereby forming a blend of the wax with an organopolysiloxane of increased molecular weight, and the blend of polymer and molten wax is emulsified in water in the presence of a surfactant, wherein the organopolysiloxane is polymerized via a hydrosilylation reaction between an organopolysiloxane containing alkenyl groups or alkynyl groups and an organopolysiloxane having Si—H groups in the presence of a platinum group catalyst.

* * * * *